United States Patent
Holper et al.

(10) Patent No.: US 9,717,890 B2
(45) Date of Patent: *Aug. 1, 2017

(54) DRAINAGE SYSTEM FOR CEREBROSPINAL FLUID

(71) Applicant: Möller Medical GmbH & Co. KG, Fulda (DE)

(72) Inventors: Manfred Holper, Rosenheim (DE);
Christoph Traxler, Kunzell (DE);
Werner Schroter, Grobenluder (DE);
Daniela Martens, Fulda (DE); Bernd M Holper, Kunzell (DE)

(73) Assignee: Möller Medical GmbH, Fulda (DE)

( * ) Notice: Subject to any disclaimer, the term of this patent is extended or adjusted under 35 U.S.C. 154(b) by 69 days.

This patent is subject to a terminal disclaimer.

(21) Appl. No.: 14/076,543

(22) Filed: Nov. 11, 2013

(65) Prior Publication Data

US 2014/0066903 A1    Mar. 6, 2014

Related U.S. Application Data

(63) Continuation of application No. 11/818,893, filed on Jun. 15, 2007, now Pat. No. 8,608,716, and a
(Continued)

(51) Int. Cl.
*A61M 27/00* (2006.01)
*A61M 1/00* (2006.01)
(Continued)

(52) U.S. Cl.
CPC ........ *A61M 27/006* (2013.01); *A61M 1/0023* (2013.01); *F04B 43/1253* (2013.01);
(Continued)

(58) Field of Classification Search
CPC .. A61M 27/00; A61M 27/002; A61M 27/006; A61M 1/0025; A61M 1/0027
(Continued)

(56) References Cited

U.S. PATENT DOCUMENTS

| 4,902,277 A | 2/1990 | Mathies et al. |
| 4,904,237 A * | 2/1990 | Janese ............... A61M 1/30 604/28 |

(Continued)

FOREIGN PATENT DOCUMENTS

| EP | 0306445 | 3/1989 |
| EP | 0448909 | 11/1993 |

(Continued)

OTHER PUBLICATIONS

Yoon, et al., "Micro devices for a cerebrospinal fluid (CSF) shunt system", Sensors and Actuators A 110 (2004) 68-76.
(Continued)

*Primary Examiner* — Lynne Anderson
(74) *Attorney, Agent, or Firm* — Klauber & Jackson LLC

(57) ABSTRACT

The object of providing a cerebrospinal fluid drainage system 1 which reacts precisely to changes in pressure in the cerebrospinal fluid, with ease of operation, is achieved by the present invention in that a pump 5 is used for draining the cerebrospinal fluid (liquor), wherein operating measured values supplied by sensors act as controlled variable for the operation of the pump. The pressure in the liquor line currently measured by a pressure sensor 10, the liquor pressure in the intracranial cavity being treated, measured intracorporeally by a pressure sensor, and/or the volume of liquor already pumped out, as operating measured value, can, for example, serve as the basis for operational control of the pump of the liquor drainage system. The liquor drainage system according to the invention has the advantage that the liquor is drained not only simply on the basis of the excess pressure in the intracranial cavity being treated, but is actively pumped out of the intracranial cavity in a controlled manner, in particular with constant measurement of the liquor pressure. In this way the pumping capacity can be regulated depending on requirement and the drainage
(Continued)

pressure or the liquor pressure kept reliably within a specific pressure range.

50 Claims, 1 Drawing Sheet

Related U.S. Application Data continuation of application No. PCT/EP2006/002730, filed on Mar. 24, 2006.

(51) Int. Cl.
  *F04B 43/12* (2006.01)
  *A61B 5/03* (2006.01)
(52) U.S. Cl.
  CPC ............ *A61B 5/031* (2013.01); *A61M 1/0031* (2013.01); *A61M 2210/0693* (2013.01); *F04B 2205/01* (2013.01)
(58) Field of Classification Search
  USPC .......................................... 604/9, 317, 318
  See application file for complete search history.

(56) References Cited

U.S. PATENT DOCUMENTS

| | | |
|---|---|---|
| 5,000,733 A | 3/1991 | Mathies et al. |
| 5,131,823 A | 7/1992 | Guignard |
| 5,195,536 A | 3/1993 | Silva et al. |
| 5,492,455 A | 2/1996 | Durham et al. |
| 5,683,357 A | 11/1997 | Magram |
| 5,739,508 A | 4/1998 | Uber, III |
| 6,105,582 A | 8/2000 | Pranevicius |
| 6,248,080 B1 | 6/2001 | Miesel et al. |
| 6,336,924 B1 | 1/2002 | Lecuyer et al. |
| 8,608,716 B2 * | 12/2013 | Holper ................ A61M 1/0023 604/318 |
| 2002/0038392 A1 | 3/2002 | De La Huerga |
| 2003/0004495 A1 | 1/2003 | Saul |
| 2003/0216666 A1 * | 11/2003 | Ericson ................ A61B 5/0031 600/561 |
| 2004/0030279 A1 | 2/2004 | Rubenstein |

FOREIGN PATENT DOCUMENTS

| | | |
|---|---|---|
| EP | 0 982 048 A1 | 3/1998 |
| EP | 0982048 | 3/2000 |
| EP | 1382291 | 1/2004 |
| JP | 2001-192333 | 7/2001 |
| JP | 2002-107259 | 4/2002 |
| JP | 2003-016357 | 1/2003 |
| JP | 2005-131369 A | 5/2005 |
| JP | 2005300941 | 10/2005 |
| JP | 2008-524367 | 7/2008 |
| JP | 2008524367 | 7/2008 |
| WO | 98/02202 | 1/1998 |
| WO | 9802202 | 1/1998 |
| WO | 0207596 | 1/2002 |
| WO | WO 02/07596 A1 | 1/2002 |
| WO | 2006014764 | 2/2006 |
| WO | WO 2006/014764 A3 | 2/2006 |

OTHER PUBLICATIONS

Yoon H J et al, Micro devices for a cerebrospinal fluid (CSF) system, (Feb. 1, 2004), Sensors and Actuators A., Elsevier Sequoia S.A., Lausanne, CH, pp. 68-72, XP004486548 ISSN:0924-4247.

* cited by examiner

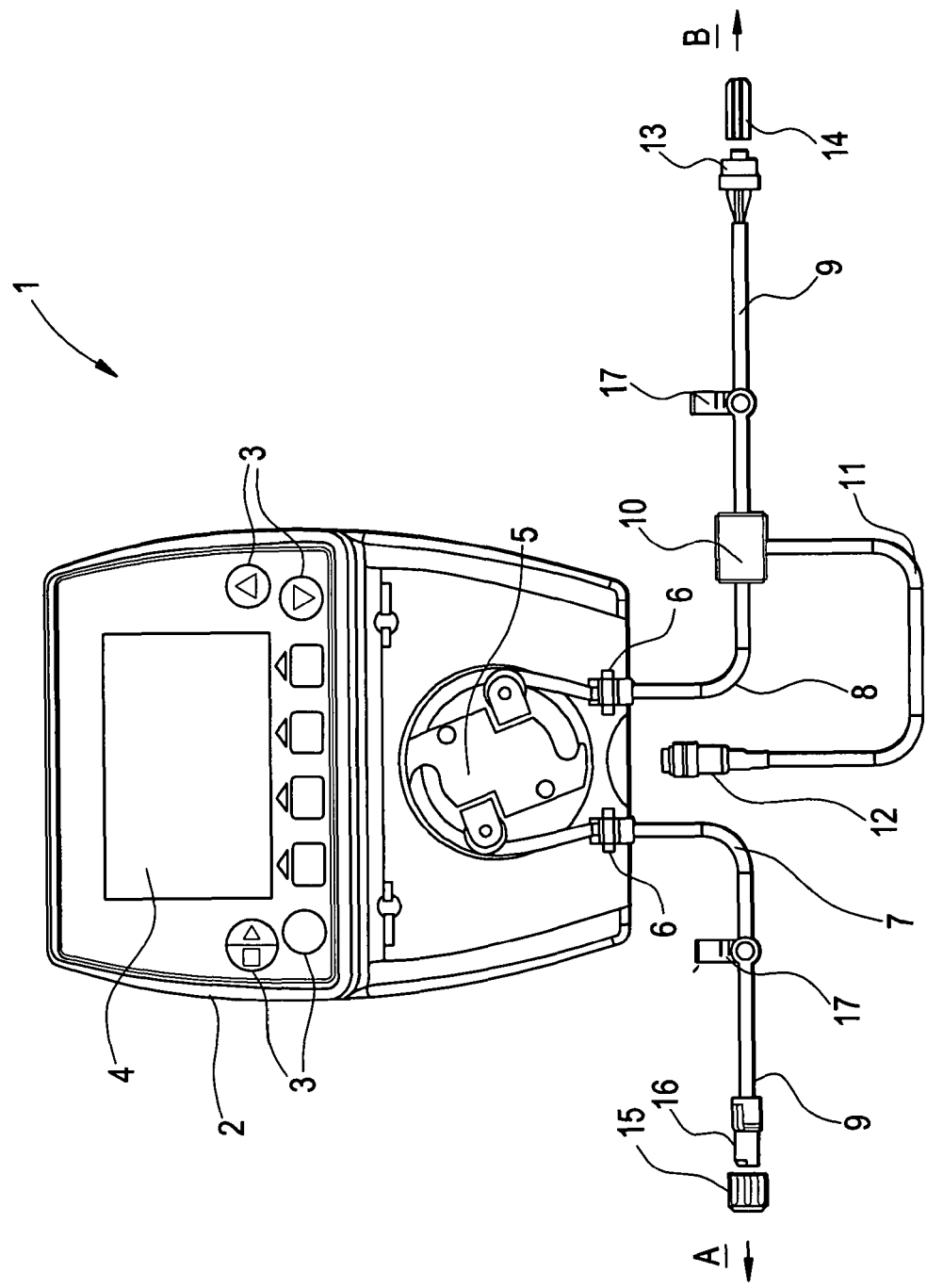

DRAINAGE SYSTEM FOR CEREBROSPINAL FLUID

CROSS REFERENCE TO RELATED APPLICATIONS

The present application is a Continuation of co-pending application Ser. No. 11/818,893, filed Jul. 15, 2007 which is a Continuation of Application No. PCT/EP2006/002730, filed Mar. 24, 2006, which in turn, claims priority from European Application No. 05016789.9, filed Aug. 2, 2005. Applicants claim the benefits of 35 USC §120 as to the PCT application, and priority under 35 USC §119 as to the European Application, and the entire disclosures of all these applications are incorporated herein in their entireties.

BACKGROUND OF THE INVENTION

The invention relates in general to a device for the drainage of cerebrospinal fluid and in particular to a drainage system comprising a fluid (liquor) drainage line, a fluid pressure sensor, and a pump for pumping out said fluid.

In patients with hydrocephalus and/or increased intracranial pressure the surplus cerebrospinal fluid (liquor cerebrospinalis or in abbreviated form "liquor") is either drained into any body cavity or into the blood by internal drainage devices or drained to the outside by external drainage devices. A liquor drainage arrangement normally consists of a brain catheter, which is inserted into the intracranial cavity (ventricle) to be treated through a hole in the skull and connected to a drainage line to the outside or to the desired body cavity or vein.

The formation of cerebrospinal fluid is about 500 ml/day, the pressure of the liquor in the lumbar region of the brain and in the brain ventricles having a constant value within defined limits. The drainage device is to be used in the treatment of hydrocephalus to produce reduced pressure of the cerebrospinal fluid in the patient's skull, wherein the lower pressure of the cerebrospinal fluid (liquor pressure) aimed at during treatment should be below the blood pressure of the brain.

An external liquor drainage arrangement is known, for example, from DE 296 21 904 U1, in which a so-called balancing chamber, where the drained fluid is collected and its volume determined, is attached to a height-adjustable stand. Owing to the sensitivity to pressure of the brain, it is extremely important in the drainage of cerebrospinal fluid or liquor to maintain a preset drainage pressure. The balancing chamber of the known liquor drainage arrangement therefore has to be precisely aligned to a specific height in relation to the patient's head. Provided in the liquor line is a pressure measurement converter, which measures the current pressure of the cerebrospinal fluid in the liquor line. The drainage pressure and therefore the hydrostatic pressure in the drainage line and the balancing chamber should, thus, not exceed or drop below specific limit values. If the patient's head position is changed, for example by swiveling the back of the bed, the balancing chamber and the pressure measurement converter must also be adjusted in height, so that on the one hand the pressure measurement is correct and on the other hand the pressure limit values are met.

DE 103 17 308 describes a liquor drainage arrangement which is likewise arranged on a height-adjustable stand, with a balancing chamber fixed to the stand, a liquor feed line connected to the balancing chamber, a pressure measurement converter in the liquor feed line and a positioning device for adjusting the height position of the stand. In the device disclosed in DE 31 27 882 a valve with a specific closing pressure is used to control the process for discharging the liquor. The operating pressure of the valve in the drainage device, thus, corresponds to the desired liquor pressure. Discharge of the cerebrospinal fluid from the ventricles takes place all the time the liquor pressure is above the switching pressure of the valve. DE 693 31 185 discloses monitoring of the pressure with optical sensor means.

U.S. Pat. No. 6,336,924 B1 discloses a liquor drainage arrangement, discharge of the liquor fluid into a collecting container being controlled by a valve which opens at a specific pressure. The liquor can again discharge only on the basis of the difference in the hydrostatic pressure between the brain ventricle and the collecting container and is not actively pumped out. This results in the disadvantage that, with this known liquor drainage system the amount of liquor draining out is also determined by the difference in height between the ventricular catheter and the collecting container. If, for example, the collecting container is arranged at the same height as the inserted ventricular catheter or even above the intraventricular catheter, no or insufficient liquor can drain out, even if there is increased intracranial pressure. Since this known arrangement is an open system when the valve is open, it is not the ventricular pressure which is measured by the pressure sensor attached after the intraventricular catheter, but the pressure in the collecting container. Therefore a pressure measurement in the described structure according to the prior art is possible only when the valve is closed. In addition, volume-controlled drainage is not possible with this known liquor drainage system.

The liquor drainage arrangements known to date have the disadvantage that they have a complicated structure and adaptation of the discharge amount to changed pressure circumstances in the liquor feed line have to be performed either by mechanical means or manually. This is also associated with corresponding inaccuracies.

SUMMARY OF THE INVENTION

The object of the invention is therefore to improve an initially mentioned drainage system to the effect that, with an easily operated structure, it reacts more precisely to pressure changes in the liquor line.

This object is achieved by a device and system for the drainage of cerebrospinal fluid, comprising a fluid drainage line (or liquor feed line), a fluid pressure sensor and a pump adapted to pump out said fluid in accordance with preset operating parameters and measured operating values, and by a method for operating the said device and system, which comprises determining a measured operating value for the pump, comparing the measured operating value against a preset operating parameter, and then operating the said pump as a function of the result of said comparison. Additional advantageous configurations and corresponding features of the respective embodiments of the invention are set forth herein and in the claims.

The basic principle of the invention consists substantially of an advantageous combination of two components, namely employing a pump to drain the cerebrospinal fluid or the liquor, and using the operating measured values supplied by sensors as a controlled variable for operating the pump. It is therefore possible, for example, to use the pressure in the liquor line currently being measured by a pressure sensor as operating measured value to form the basis for controlling the pump. Additionally or alternatively, the pressure measured by an intracorporeal pressure sensor in the intracranial cavity of the patient being treated can be used as an operating measured value for controlling the pump. The pressure measurement may here be done by the intracorporeally installed pressure sensor, for example in a ventricle or in the parenchyma. The volume of liquor already pumped out can also further serve as the basis for operational control of the pump of the present fluid drainage system.

Consequently the liquor drainage system according to the invention has the advantage, compared with known devices, that the cerebrospinal fluid is not simply drained on the basis of the excess pressure in the intracranial cavity being treated, but the liquor is actively pumped out of the intracranial cavity in a controlled manner, in particular with constant measurement of the liquor pressure. In this way the pumping capacity can be regulated depending on requirement and the drainage pressure or the liquor pressure kept reliably within a specific range. Either the excorporeally measured pressure in the liquor (drainage/feed) line and/or the liquor pressure measured by an intracorporeal pressure sensor in the patient's skull and/or the volume of liquor already pumped out here acts as the basis for operational control of the liquor drainage system. With the liquor drainage system according to the invention the requirement existing to date in arrangements according to the prior art for a specific height setting of the arrangement and a valve device or other susceptible mechanical components is no longer used or required.

According to a preferred embodiment of the present invention a drainage pumping system for cerebrospinal fluid (or liquor) is provided, which can pump out a specific volume of liquor in a targeted manner with a pressure-controlled pump. Since the liquor feed line or the brain catheter is directly connected to the intracranial cavity (ventricle) to be treated, the same pressure prevails in the liquor feed line and in the intracranial cavity to be treated, which is determined by the pressure sensor arranged in the liquor feed line. For reasons of safety and accuracy of the liquor pressure measurement it is also conceivable to provide several pressure sensors, so that, for example, false or missing measured values from a defective pressure sensor can be replaced by the measured values of an intact pressure sensor. In the case of several pressure sensors, their measured values can be balanced out with one another, in order to check or improve the measurement accuracy. It is, thus, particularly advantageous for the accuracy of the pressure measurement if the pressure of the cerebrospinal fluid is measured directly via an intracorporeal pressure sensor in the patient's intracranial cavity and the measured value is taken into consideration as a basic parameter for controlling the liquor drainage system according to the invention. The pressure measurement can be performed particularly reliably if the intracorporeal pressure sensor is placed, for example, in a ventricle or in the parenchyma. Moreover, false measurements caused by slit ventricles or catheter occlusion can be avoided by the intracorporeal sensor application according to the present invention.

If the intracranial pressure or the pressure of the cerebrospinal fluid (liquor) rises above a defined upper value, the pump is preferably automatically activated and a specific volume of liquor pumped out until the desired pressure of the cerebrospinal fluid is reached. This process is actively monitored via the pressure sensor(s) installed in the liquor feed (fluid drainage) line and/or via the pressure sensor arranged in the patient's skull. As soon as an adequate volume of cerebrospinal fluid has been pumped out and it is established via a pressure sensor that the cerebrospinal fluid pressure has fallen to a defined lower value again, the pump can be automatically stopped.

As already mentioned above, it is advantageous for the accuracy of the pressure measurement if it is performed intracorporeally by a pressure sensor arranged in the intracranial cavity being treated. If the pressure measurement takes place only outside the patient's body in a liquor line, the cerebrospinal fluid pressure can be measured all the more precisely, the closer the pressure sensor is arranged to the skull opening. The accuracy of the measurement of the cerebrospinal fluid pressure is further improved if the pressure sensor is located as far as possible at the same height as the geometric center of the cranial cavity. According to a further advantageous embodiment of the present invention the pressure sensor in the liquor feed line is therefore equipped with fastening means which enable arrangement of the pressure sensor in the patient's head region. The pressure sensor may, for example, be fastened via a headband close to the skull hole or arranged on the patient's ear via an ear bracket or a clip. A further possibility for fastening a pressure sensor in the patient's head region is the use of clipped-on ECG adhesive pads at the desired measuring position on the temple or behind the patient's ear or an ECG adhesive electrode near the ear. It can be seen as a further advantage that the adhered or clipped-on sensor cannot slip and no malfunctions in the blood supply to the skin are caused by clamping or the contact pressure of a rubber band.

Control of the liquor drainage system is advantageously done by an electronic control unit. In the electronic control unit the calculations required for operating the pump are performed on the basis of the preset operating parameters and the operating measured values or the measured operating data. The electronic control unit of the liquor drainage system is preferably programmable, so that specific operating cycles can be performed, for example for different medical applications, via appropriate software. It is further possible to set up alarm functions in the electronic control of the liquor drainage system, which give the alarm by optical and/or acoustic means if there is a deviation of the measured operating data from a preset range for the pressure or the pumping volume. An alarm signal of this kind is advantageously also transmitted electronically to an external monitoring unit via an appropriate interface. With simultaneous use of a patient monitor, the electronic control unit of the liquor drainage system according to the invention can also, via an interface, issue an electronically pre-processed measuring signal, which can be evaluated by the external patient monitor.

According to a preferred embodiment of the present invention the liquor drainage system comprises input means, via which specific operating parameters, such as, e.g. preset pressure limit values of the liquor pressure or the cerebrospinal fluid pressure in the ventricle to be treated, can be input into the control electronics. In the control electronics electronic memory means can also be provided, in which, for example, specific operating cycles of the liquor drainage system can be stored or kept available. The liquor drainage system may further comprise operating elements, via which the operation of the pump can be directly controlled. This provides the possibility of also controlling the pump manually, for example to generate a higher pumping capacity on short-term to eliminate blockages.

The pressure sensor in the liquor feed line is preferably constructed as an electronic pressure sensor, which transmits the pressure measured in the liquor feed line to the control electronics in the form of electric signals. The pressure sensor arranged in the skull, in particular in a ventricle or in the patient's parenchyma is also preferably constructed as an electronic pressure sensor, which transmits the measured cerebrospinal fluid or liquor pressure in the patient's skull to the control electronics in the form of electric signals. On the basis of the pressure signals supplied by the pressure sensor and the preset pressure limit values, the control electronics calculate the required operation of the liquor drainage system or the operation of the liquor pump. The control electronics, thus, carry out in particular a comparison between the preset liquor pressure limit values and the pressure in the liquor feed line determined by the pressure sensor. On the basis of the calculation, the control electronics decide whether the pump of the liquor drainage system should be activated or deactivated and/or with what pumping capacity and possibly over what time period the liquor drainage pump should be operated. Naturally the liquor drainage system according to the invention can also be used simply for intracorporeal and/or extracorporeal measurement of the cerebrospinal fluid or liquor pressure, without operation of the liquor drainage pump.

A hose pump, which has the advantage that the pumped fluid inside the hose system does not come into contact with any foreign bodies, is preferably used as pump. For the pressure measurement a piezoresistive pressure sensor in a micromechanical embodiment is particularly suitable. These pressure sensors are small in design and highly sensitive with comparatively low production costs. During the pressure measurement the sensor generates an electric signal which is proportional to the pressure to be measured. Piezoresistive sensors typically contain a silicon chip as sensor element, on the front of which the ambient pressure acts directly. In the present application the pressure of the liquor is transmitted to the back of the chip via a silicon gel. The difference between the ambient pressure and the pressure of the liquor causes the membrane of the chip to arch and the thus arising mechanical stresses are converted into a change in the measurement resistance in the sensor element. Because of the configuration of piezoresistive pressure sensors as a measuring bridge, an output voltage signal is generated which is proportional to the feed voltage of the sensor in the manner of a ratiometric sensor and to the differential pressure.

To connect the individual fluid-carrying components the liquor drainage system according to the invention is equipped with a hose system with appropriate branches. This hose system comprises a liquor feed line or a brain catheter, leading from the patient's head to the pump, and a liquor drainage line, leading from the pump to a collecting bag for collecting the drained liquor.

By contrast with the liquor drainage arrangements known from the prior art, in which liquor discharges into a collecting container only by its own hydrostatic pressure, in the system according to the invention the liquor is pumped out in a targeted manner, the volume pumped out being regulated by pressure control. In this way it is possible to set freely the volumes of liquor and intracranial pressure values via which the pumping process is regulated. Additionally, generation of a pressure in the hose system below a defined lower limit is possible, in order, e.g. to check the ability to penetrate the hose system or to remove foreign bodies (e.g. blood coagulum) blocking the hose system. In this way purely volume-controlled liquor drainage, as required for continuous lumbar drainage, for example, can be carried out with the liquor drainage system according to the invention.

The hose system of the liquor drainage system according to the invention is a closed hose system which enables simultaneous measurement of the pressure via the pressure sensor during the pumping process. Therefore, e.g., disconnections of the hose connections owing to an acute drop in pressure in the hose system or hose occlusions or hose blockages because of very low or very high pressure values can be detected by the pressure sensor during the pumping process.

According to a further preferred embodiment of the present invention the operating data of the liquor drainage system are detected continuously or at intervals. For example, the liquor drainage volume can be continuously calculated from the rotation of the pump and the hose diameter. Thereby, recording and documenting the chronological course of the pumping volume determined and the pressure in the liquor feed line can be done. These data can be transmitted to an evaluation unit for further evaluation by the control electronics of the present drainage system. This enables automated evaluation of the chronological course of the intracranial pressure and liquor drainage, which was possible in former systems only by reading the fluid level on the collecting bag.

The operating data of the liquor drainage system, such as, e.g. the recording and documentation of the chronological course of the pumping volume determined, the liquor pressure in the patient's skull determined by the respective pressure sensors or the pressure in the liquor feed line, the operational life of the pump, the total volume delivered by the pump, the operating mode or the operational life of the pump can advantageously be stored in the electronic memory means of the liquor drainage system according to the invention and retrieved. To guarantee data security, input means may be provided with which the data filed in the memory means of the liquor drainage system can be manually deleted. The liquor drainage system according to the invention advantageously has an optical display via which set operating parameters and/or current measured values of operating data can be displayed.

The data transmission from the liquor drainage system to an external evaluation unit is done via an interface, such as, e.g. a cable, infrared or radio connection or with the aid of a memory card/chip. The liquor drainage system according to the invention may be further equipped with an additional output for transmitting operating data, in particular the liquor pressure signal, to external display monitors and with a call button for the service personnel. In order to guarantee mains-independent operation (for example in the event of a power outage), the liquor drainage system is preferably equipped with a store for electric energy or an accumulator which ensures mains-independent operation for at least a few hours and facilitates transport of the patient with the system.

Further details, preferred embodiments and advantages of the present invention emerge from the following description, with reference to the drawing.

BRIEF DESCRIPTION OF THE DRAWING

FIG. 1 shows a sketch of the structure of a liquor drainage system according to a preferred embodiment of the present invention.

DETAILED DESCRIPTION OF THE INVENTION

The embodiment of the liquor drainage system 1 shown in FIG. 1 comprises, according to the present invention, a main component 2 with a housing 2, in which an electronic control unit with electronic means for the above-described calculations is accommodated. Arranged on the housing 2 are input and operating elements 3, via which operating parameters required for the operation of the liquor drainage system 1 or a desired operating mode of the liquor drainage system 1 can be manually input. All the input operating parameters and/or current operating measured values and operating modes of the liquor drainage system 1 can be displayed via a display 4.

The main component 2 of the liquor drainage system 1 further comprises a hose pump 5 with connectors 6 for hose connections 9 of a hose system. The hose connections 9 connected to the hose pump 5 are on the one hand a liquor feed line (brain catheter) 8 between the hose pump 5 and the patient and on the other hand a hose connection 7 between the hose pump 5 and a drainage bag (not shown) in which the pumped out cerebrospinal fluid (liquor) collects. In the FIGURE, arrow A indicates the connecting direction of hose connection 7 to the drainage bag and arrow B the connecting direction of hose connection 8 to the patient. For purposes of illustration and not limitation, it has proved advantageous if the hose connections 9 of the hose system have an inner diameter of approximately 1.0 mm, an outer diameter of approximately 4.0 mm, a wall thickness of approximately 1.5 mm and a hardness in the range of 50-55 Shore A.

The hose pump 5 is constructed in a known way and comprises a flexible pump hose segment arranged in the shape of a circle. In the center of the pump hose segment arranged in the shape of a circle, the axle of a pump rotor is positioned, on the radially outer ends of which rotatably positioned rollers are provided. As the pump rotor rotates, the rollers roll down on the circular pump hose segment, wherein the pump hose segment is pressed together. Any fluid located in the pump hose segment is conveyed in the direction of rotation of the pump rotor by the rotational movement of the pump rotor with the rollers rolling down on the pump hose segment. A hose pump of this kind has the advantage that the fluid located in the hose does not come into contact with foreign bodies and contamination of the fluid is therefore ruled out. A further advantage of the hose pump is that the liquor feed line (liquor hose) 8 is closed in all rotational positions of the pump rotor by the rotor rollers, positioned via a pressure spring, in such a way that there is no question of uncontrolled draining of the liquor fluid.

Arranged on the hose connection (brain catheter or liquor feed line) 8 between the hose pump 5 and the patient is a pressure sensor 10, which measures the pressure of the liquor in the liquor feed line 8 constantly or at intervals. The pressure measured values determined by the pressure sensor are converted into electric signals and transmitted via an electric cable 11 to the electronic control unit in the main component 2 of the liquor drainage system 1. For this purpose the electric cable 11 from the pressure sensor 10 is connected via a connector 12 to the main component 2 of the liquor drainage system 1 via an appropriate interface (not illustrated).

Additionally or alternatively, the pressure of the cerebrospinal fluid can be measured constantly or at intervals directly in the intracranial cavity being treated via a pressure sensor (not illustrated) arranged in the patient's head. The pressure measured values determined by the pressure sensor are likewise converted into electric signals and transmitted to the electronic control unit of the liquor drainage system 1 via an electric cable and an appropriate interface.

The electronic control unit of the liquor drainage system 1 uses the operating measured values of the pressure in the liquor feed line 8, transmitted by the pressure sensor(s) (10) as the basis for the calculations in the electronic control unit for regulated operation of the hose pump 5. If, via the pressure sensor 10, a pressure is established in the liquor feed line 8, for example, which is above a preset operating parameter or outside a specific pressure range, the electronic control unit of the liquor drainage system 1 can activate the hose pump 5.

The electronic control unit continuously monitors the pressure in the liquor feed line 8 during the pumping process via the pressure sensor 10. As soon as the pressure in the liquor feed line 8 has reached a preset operating parameter or has reached or dropped below a specific lower limit value of the pressure in the liquor feed line 8, the electronic control unit can set the operation of the hose pump 5. Additionally or alternatively, the electronic control unit can monitor the pressure of the cerebrospinal fluid during the pumping process via the intracorporeal pressure sensor in the patient's skull. As soon as the cerebrospinal fluid pressure has reached a preset operating parameter or has reached or dropped below a specific lower limit value of the cerebrospinal fluid pressure, the electronic control unit can set the operation of the hose pump 5.

The liquor drainage system 1 may additionally contain detection means which determine the delivered volume of the liquor and use the drained volume of liquor as the basis for controlling the pump 5. The number of revolutions of the pump rotor may be involved in this, for example, since this is in direct proportion to the volume delivered by the hose pump 5.

Both the hose connection 7 between the hose pump 5 and the drainage bag and the liquor feed line 8 between the hose pump and the patient may be equipped with a branch, for example in the form of a three-way tap 17, via which further hose lines can be connected to the hose system. The hose connections 9 are connected to further hose segments or other liquor fluid-carrying components of the liquor drainage system 1 in each case via suitable hose connecting elements 13, 14, 15, 16.

The hose connecting elements or hose couplings 13, 14, 15, 16 are constructed in each case in such a way that they guarantee pressure-proof connection of the hose connections and therefore a closed hose system. The hose connecting elements or hose couplings 13, 14, 15, 16 may additionally be constructed in such a way that they ensure once-only use of the hose connections 7, 8 or of the entire hose set, i.e. a hose connection 7, 8 can be used only once in the closed hose system, in order to guarantee its sterility. Additionally or alternatively, the hose system may also be equipped with one or more electronic memory means in which the use of the hose system or the relevant hose connections 7,8 is electronically stored, so that previous use of the hose system or the hose connections 7, 8 can be established and repeated use ruled out, in order to guarantee sterility. This memory means may be integrated into the pressure sensor unit 10, for example, or into the electrical connector 12 of the electric cable 11. It is further possible for at least one connecting element 13, 14 of the hose system to be constructed in such a way that the pressure sensor 10 can be accommodated or integrated therein. In this way the pressure sensor would be accommodated in direct contact with the liquor in the drainage system and mounted as easily replaceable.

In this way it can be ensured that the pressure measured by the pressure sensor 10 in the liquor feed line 8 at the measuring point also matches the pressure in the intracranial cavity being treated. For particularly reliable measurement of the cerebrospinal fluid pressure, measurement by an incorporeal pressure sensor in the patient's intracranial cavity can also be involved. The liquor drainage system 1 according to the invention is on the one hand distinguished by simple operability and on the other hand guarantees a controlled liquor drainage process, in which the drained volume of liquor is regulated depending on requirement and the drainage pressure or the liquor pressure can be maintained reliably within a specific pressure range.

While the invention has bee described and illustrated herein by reference to the specific embodiments, various specific materials, procedures and examples, it is understood that the invention is not restricted to the various materials, combinations of materials or components, and procedures selected for that purpose. Indeed, various modifications of the invention in addition to those described herein will become apparent to those skilled in the art from the foregoing description and the accompanying FIGURE. Such modifications are intended to fall within the scope of the appended claims.

The invention claimed is:

1. A drainage system for the drainage of cerebrospinal fluid (CSF), comprising
   a CSF feed line,
   a pressure sensor, wherein the pressure sensor is operable to determine pressure in the CSF feed line, or CSF pressure intracorporeally,
   a pump that automatically pumps out the cerebrospinal fluid during drainage as a function of one or more preset operating parameters and one or more measured operating values,
   and a detection means operable to detect the flow or volume of CSF pumped out, wherein the one or more measured operating values comprises at least the pressure determined in the CSF feed line or the CSF pressure determined intracorporeally, wherein the preset operating parameters and the measured operating values allow for an automated control of the drainage process.

2. A system according to claim 1, wherein the one or more preset operating parameters or measured operating values comprises the pressure measured in the CSF feed line or the volume of liquor pumped out.

3. A system according to claim 1, wherein the one or more preset operating parameters or measured operating values comprises the CSF pressure measured intracorporeally in an intracranial cavity being treated.

4. A system according to claim 1, wherein the pump is constructed as a hose pump.

5. A system according to claim 1, wherein the CSF drainage system comprises an intracorporeal pressure sensor operable to determine the CSF pressure directly in an intracranial cavity being treated.

6. A system according to claim 5, wherein the intracorporeal pressure sensor is constructed as an electronic pressure sensor which converts changes in the CSF pressure in the intracranial cavity being treated into electric pulses.

7. A system according to claim 6, wherein the intracorporeal pressure sensor is constructed as piezoresistive pressure sensor which converts changes in the liquor pressure in the intracranial cavity being treated into electric pulses.

8. A system according to claim 5, wherein the pressure sensor is connected, attached, or mounted to or onto an adhesive pad or ECG adhesive electrode which is arranged on the patient's temple.

9. A system according to claim 5, wherein the pressure sensor is connected, attached, or mounted to or onto an adhesive pad or ECG adhesive electrode which is arranged behind the patient's ear.

10. A system according to claim 1, wherein the pressure sensor operable to determine the pressure in the CSF feed line (8) is constructed as a piezoresistive pressure sensor.

11. A system according to claim 10, wherein the pressure sensor is arranged near the patient.

12. A system according to claim 10, wherein the pressure sensor is arranged on the CSF feed line (8) substantially at the same height as the geometric center of the intracranial cavity.

13. A system according to claim 10, wherein the pressure sensor is provided with fastening means.

14. A system according to claim 13, wherein the pressure sensor is provided with fastening means which enable the pressure sensor to be arranged on the patient's ear.

15. A system according to claim 10, wherein several pressure sensors are provided.

16. A system according to claim 10, wherein the pressure sensor is constructed as an electronic pressure sensor, which converts changes in pressure in the CSF feed line into electric pulses.

17. A system according to claim 16, wherein the electronic pressure sensor is a piezoresistive pressure sensor.

18. A system according to claim 1, wherein the detection means monitors the volume of CSF pumped out and the pressure sensor monitors the pressure in the CSF feed line continuously or at intervals.

19. A system according to claim 1 wherein the detection means is an electronic control unit that performs calculations required for the pump to operate on the basis of the preset operating parameters and the measured operating values.

20. A system according to claim 19, wherein the electronic control unit is programmable in such a way that specific operating cycles can be carried out.

21. A system according to claim 19, wherein the electronic control unit comprises alarm functions which are activated if there is a deviation of a measured operating measured value from the corresponding preset operating parameter.

22. A system according to claim 19, wherein the electronic control unit comprises at least one interface, via which measured operating values or operating parameters can be transmitted to an external monitoring system, an external display device or a patient monitor.

23. A system according to claim 22, wherein the at least one interface is a cable, infrared or radio connection or a removable memory card/chip.

24. A system according to claim 19 wherein the electronic control unit comprises electronic memory means in which preset operating cycles of the CSF drainage system or chronological documentation of the operation of the CSF drainage system can be stored.

25. A system according to claim 19 further comprising an input means via which operating parameters can be input into the electronic control unit.

26. A system according to claim 25, wherein the operating parameters are selected from the group consisting of preset pressure limit values of the liquor pressure in the liquor feed line or preset pressure limit values of the liquor pressure in the intracranial cavity being treated.

27. A system according to claim 1 further comprising one or more operating elements via which the operation of the pump can be directly controlled or an alarm function can be manually activated.

28. A system according to claim 1 further comprising an optical display, via which set operating parameters and/or current operating measured values can be displayed.

29. A system according to claim 1 further comprising a store for electric energy or an accumulator for mains-independent power supply.

30. A system according to claim 1, further comprising a closed hose system with closed hose connections for connecting the fluid-carrying components.

31. A system according to claim 30, wherein the closed hose system comprises means which ensure that the hose connections can be used once only.

32. A system according to claim 31, wherein the pressure sensor is integrated into one of the connecting elements.

33. A system according to claim 31, wherein the means are connecting elements.

34. A system according to claim 30, wherein the hose system is equipped with at least one electronic memory medium in which use of the hose system and/or relevant hose connections is electronically stored, so that previous use of the hose connections can be established and repeated use ruled out, in order to guarantee sterility.

35. A system according to claim 1 further comprising a drainage bag for collecting drained cerebrospinal fluid.

36. A system according to claim 1 wherein the preset operating parameters comprise a specific lower limit value of the pressure in the CSF feed line or a specific lower limit value of the intracorporeal cerebrospinal fluid pressure, and wherein operation of the pump is automatically set as the pressure in the CSF feed line or the intracorporeal CSF pressure reaches or drops below said specific lower limit value.

37. A system according to claim 1, wherein the preset operating parameters comprise a specific upper limit value of the pressure in the CSF feed line or a specific upper limit value of the intracorporeal cerebrospinal fluid pressure, and wherein operation of the pump is activated as the pressure in the CSF feed line or the intracorporeal CSF pressure rises above the upper limit value.

38. A system according to claim 1, wherein the detection means is an electronic control unit.

39. Method for operating a drainage system according to claim 1, comprising the following steps: determining a specific operating measured value comparing the determined operating measured value with a preset operating parameter specifically operating the pump as a function of the result of the comparison between the determined operating measured value and the preset operating parameter.

40. Method according to claim 39, wherein the preset operating parameters comprise one or more limit values or a range for the pressure measured in the liquor feed line.

41. Method according to claim 39, wherein the preset operating parameters comprise one or more limit values or a range for the liquor pressure measured intracorporeally in the intracranial cavity being treated.

42. Method according to o claim 39, wherein the preset operating parameters comprise one or more limit values for the volume of liquor pumped out.

43. Method according to claim 39, wherein the operation of the pump is controlled as a function of the pressure measured in the liquor feed line.

44. Method according to claim 39, wherein the operation of the pump is controlled as a function of the liquor pressure measured intracorporeally in the intracranial cavity being treated.

45. Method according to claim 39, wherein the operation of the pump is controlled as a function of the volume of liquor pumped out.

46. Method according to claim 39, comprising the additional step: selecting a specific operating mode of the pump from a selection of operating modes as a function of the result of the comparison between the determined operating measured value and the preset operating parameter and selectively operating the pump.

47. Method according to claim 46, wherein the selection of operating modes of the pump is made from a group of the following operating modes: pump at standstill; starting the pump when a preset upper limit value for the pressure in the liquor feed line has been reached; operation of the pump for a specific period of time; operation of the pump until a specific pumping volume has been delivered or operation of the pump until a preset lower limit value for the pressure in the liquor feed line has been reached.

48. Method according to claim 39, wherein the pump is activated if the pressure in the liquor feed line rises above a defined upper value and the pump is deactivated if the desired pressure has ensued in the liquor feed line or a specific volume of liquor has been pumped out.

49. Method according to claim 39, wherein the pump is activated if the liquor pressure in the intracranial cavity being treated rises above a defined upper value and the pump is deactivated if the desired liquor pressure has ensued in the intracranial cavity being treated or a specific volume of liquor has been pumped out.

50. Method according to claim 39, wherein the operation or the operating mode of the pump can be changed or controlled on the basis of manual control via the manual input means.

* * * * *